US00PP32012P2

(12) United States Plant Patent
van Vliet

(10) Patent No.: US PP32,012 P2
(45) Date of Patent: Jul. 21, 2020

(54) ***PHILODENDRON* PLANT NAMED 'FLOPHI1901'**

(50) Latin Name: ***Philodendron* sp.**
Varietal Denomination: FLOPHI1901

(71) Applicant: Florali Licensing B.V., Rijswijk (NL)

(72) Inventor: Leendert J. van Vliet, Rijswijk (NL)

(73) Assignee: Florali Licensing B.V., Rijswijk (NL)

( * ) Notice: Subject to any disclaimer, the term of this patent is extended or adjusted under 35 U.S.C. 154(b) by 0 days.

(21) Appl. No.: 16/602,202

(22) Filed: Aug. 27, 2019

(51) Int. Cl.
*A01H 5/00* (2018.01)

(52) U.S. Cl.
USPC ..... Plt./381

(58) Field of Classification Search
USPC ..... Plt./381
CPC ..... A01H 5/00
See application file for complete search history.

*Primary Examiner* — Annette H Para
(74) *Attorney, Agent, or Firm* — Samuel R. McCoy, Jr.

(57) ABSTRACT

'FLOPHI1901' is a distinctive *Philodendron* plant which is characterized by the combination of a short plant height, a compact growth habit, and small, dark green foliage as well as the uniformity and stability of these characteristics from generation to generation.

2 Drawing Sheets

Latin name of the genus and species: The Latin name of the genus and species of the novel variety disclosed herein is *Philodendron* sp.

Variety denomination: The inventive variety of *Philodendron* disclosed herein has been given the variety denomination 'FLOPHI1901'.

BACKGROUND OF THE INVENTION

Parentage: 'FLOPHI1901' is a spontaneous whole-plant mutation which was discovered growing amongst a cultivated population of unnamed *Philodendron* sp. plants (not patented) which was discovered by the inventor in March of 2018 at a commercial greenhouse in De Kwakel, the Netherlands. The mutation was first noted for its more compact habit and smaller leaves compared to the parent plant.

Asexual Reproduction: Asexual reproduction of the new cultivar 'FLOPHI1901', by way of rooting leaf cuttings, was first initiated in March of 2018 at the inventor's commercial greenhouse in De Kwakel, the Netherlands. Through three subsequent generations, the unique features of this cultivar have proven to be stable and true to type.

SUMMARY OF THE INVENTION

The cultivar 'FLOPHI1901' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FLOPHI1901'. These characteristics in combination distinguish 'FLOPHI1901' as a new and distinct *Philodendron* cultivar:

1. *Philodendron* 'FLOPHI1901' exhibits a small plant size and a compact growth habit; and
2. *Philodendron* 'FLOPHI1901' exhibits small, elliptic to ovate foliage; and 3. *Philodendron* 'FLOPHI1901' exhibits dark green, glossy foliage.

BOTANICAL DESCRIPTION OF THE PLANT

Figure 1:
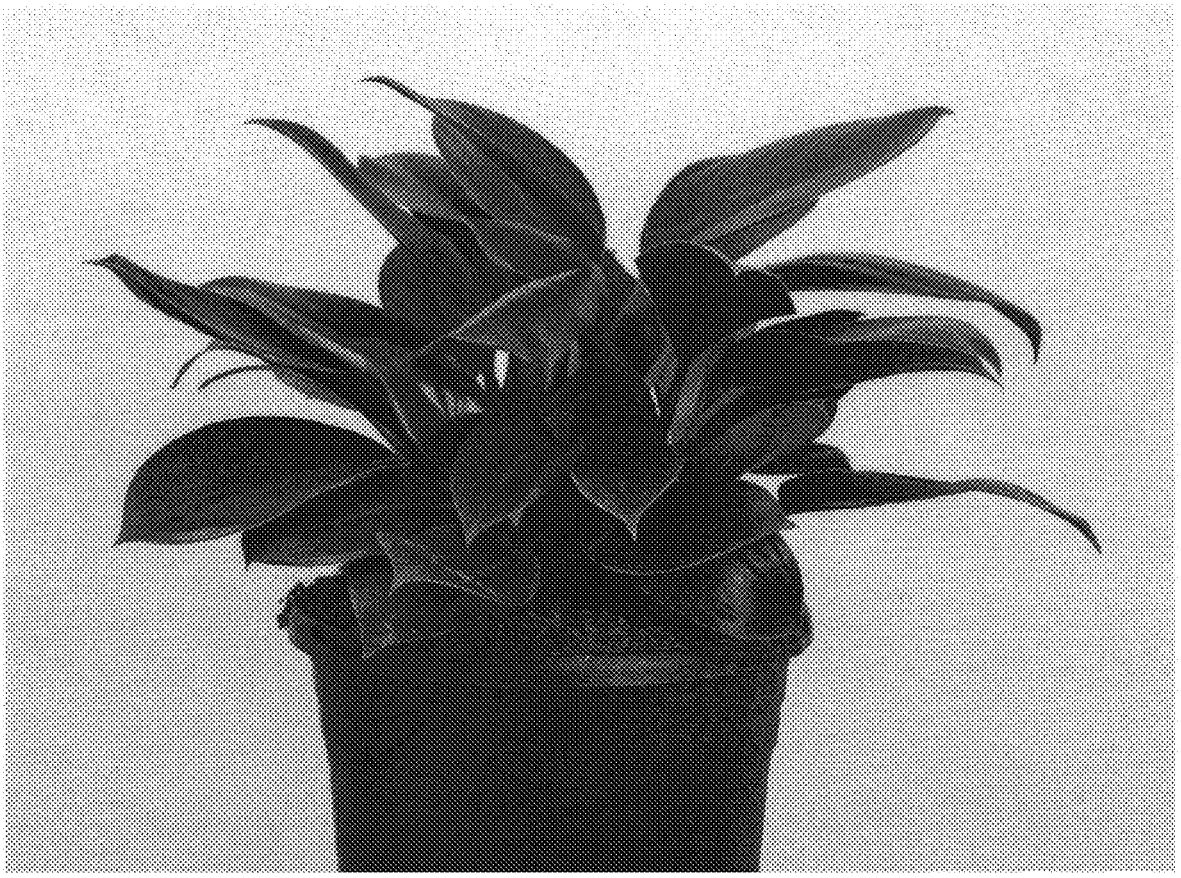
FIG. 1 illustrates, as nearly true as it is reasonably possible to make the same in color photographs of this type, an exemplary plant of 'FLOPHI1901' grown in a commercial greenhouse in De Kwakel, the Netherlands. This plant is approximately 6 months old, in a 23 cm container.
Figure 2:
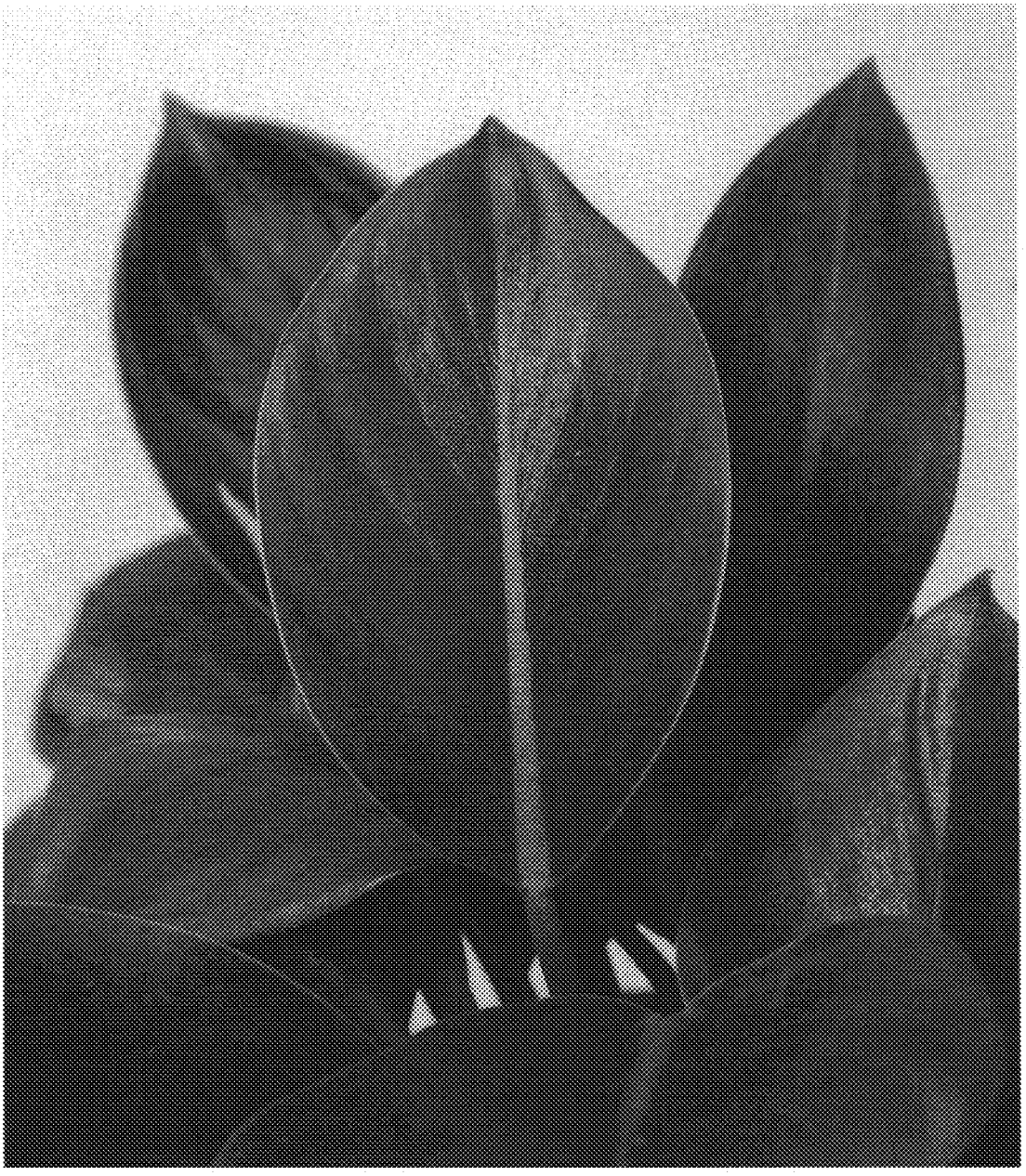
FIG. 2 illustrates, as nearly true as it is reasonably possible to make the same in color photographs of this type, the typical mature foliage of 'FLOPHI1901'.

The following observations and measurements, made in September of 2018, describe averages from a sample set of six 6 month-old 'FLOPHI1901' plants grown in 23 cm nursery containers at a greenhouse in De Kwakel, the Netherlands. Plants were produced using conventional greenhouse production protocols for *Philodendron* sp. which consisted of growing plants under shade, watering with drip irrigation, and producing plants without supplemental fertilizer, chemical pest measures, or photoperiodic treatments.

Those skilled in the art will appreciate that certain characteristics will vary with older or, conversely, with younger plants. 'FLOPHI1901' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'FLOPHI1901' and a comparison with the parent plant and most similar commercial cultivar are provided below.

Plant description:

*Growth habit*.—Compact, broad spreading to upright herbaceous perennial with foliage growth from basal shoots.

*Plant shape*.—Flattened globular.

*Height from soil level to top of foliar plane*.—23.8 cm.

*Plant spread*.—40.2 cm.

*Number of basal shoots per plant*.—8.

*Growth rate*.—Moderately fast.

*Plant vigor*.—Vigorous to very vigorous.

*Propagation*.—Type — Asexual propagation is accomplished by way of stem and leaf cuttings which root well without rooting compound or hormone. Time to initiate rooting — Approximately 14 days at 25 degrees Celsius. Time to produce a rooted cutting — Approximately 8 to 12 weeks, at an ambient temperature range of 22 to 25 degrees Celsius, are needed to produce a marketable rooted cutting.

*Disease and pest resistance or susceptibility*.—Neither susceptibility nor resistance to pests and diseases common to either *Philodendron* have been observed.

*Environmental tolerances*.—Adapt to temperatures as low as 5 degrees Celsius and at least as high as 40 degrees Celsius; moderate to high tolerance to rain; low to moderate tolerance to wind.

Roots:

*Density*.—Not very dense.

*Length*.—14.6 cm.

*Diameter*.—0.3 cm.

*Texture*.—Fleshy, non-fibrous.

*Color*.—Greyed-orange, RHS 164A.

Foliage:

*Quantity*.—7 leaves per shoot.

*Arrangement*.—Alternate.

*Attachment*.—Petiolate.

*Division*.—Simple.

*Lamina*.—Shape — Elliptic to ovate. Length — 13.9 cm, excluding the petiole. Width — 8.3 cm. Apex — Apiculate. Base — Obtuse to short attenuate. Aspect — Slightly concave. Margins — Entire and slightly angular; slightly to moderately undulate. Texture and luster, adaxial surface — Smooth, glabrous and moderately glossy. Texture and luster, abaxial surface — Smooth, glabrous and slight to moderately glossy. Color — Juvenile foliage, adaxial surface — Green, nearest to RHS 143B. Juvenile foliage, abaxial surface — Yellow-green, nearest to in between RHS 144A and 144B. Mature foliage, adaxial surface — Nearest to in between green and yellow-green, RHS NN137A and 147A. Mature foliage, abaxial surface — Nearest to in between green and yellow-green, RHS 143B and 144A. Venation — Pattern — Pinnate. Color, adaxial surfaces — Green, nearest to RHS 137B. Color, abaxial surface — Green, nearest to RHS 143B.

*Stipule*.—Position — A dry stipule is present at the base of each petiole. Shape — Narrow ovate. Apex — Narrow apiculate. Base — Attenuate. Aspect — Flattened on the upper side; otherwise rounded. Length — 5.3 cm. Width — 1.9 cm. Texture and luster, adaxial surface — Smooth, glabrous and matte. Texture and luster, abaxial surface — Smooth, glabrous and matte. Color, adaxial surface — Greyed-orange, nearest to a mixture of RHS 164B, 165A, and 165B. Color, abaxial surface — Greyed-orange, nearest to a mixture of RHS 164B, 165A, and 165B.

*Petiole*.—Attitude — Upright and outward. Strength — Strong. Aspect — Flattened on the upper side; otherwise rounded. Length — 14.3 cm. Width — 0.6 cm at the widest. Texture and luster, adaxial surface — Smooth, glabrous and slightly glossy. Texture and luster, abaxial surface — Smooth, glabrous and slightly glossy. Color, adaxial surface — Nearest to in between green and yellow-green, RHS 143A and 146A. Color, abaxial surface — Yellow-green, nearest to RHS 144A. Sheath — Shape — Deltoid. Length — 7.0 cm. Width — 0.4 cm. Margin — Entire; not undulated. Texture and luster — Smooth, glabrous and glossy. Color — Yellow-green, nearest to a mixture of RHS 144A and 144B.

Inflorescence: To date, 'FLOPHI1901' has not flowered.

Comparisons With the Parent Plants

Plants of the new cultivar 'FLOPHI1901' differ from the seed parent, an unnamed *Philodendron* sp. plant (not patented), in the characteristics described in Table 1 below.

TABLE 1

| Characteristic | 'FLOPH11901' | The parent |
|---|---|---|
| Growth habit. | More spreading. | Less spreading. |
| Abundance of foliage. | More abundant. | Less abundant. |
| Foliage attitude. | Relaxed. | Upright and outward. |
| Foliage size. | Smaller than the parent. | Larger than 'FLOPH11901'. |

Comparisons With the Closest Known Comparator

Plants of the new cultivar 'FLOPHI1901' differ from the closest known commercial comparator, *Philodendron* hybrid 'Rojo Congo' (U.S. Plant Pat. No. 14,116), in the following characteristics described in Table 2 below.

TABLE 2

| Characteristic | 'FLOPH11901' | 'Rojo Congo' |
|---|---|---|
| Plant size. | Smaller than the parent. | Larger than 'FLOPH11901'. |
| Plant height. | 23.8 cm. | 76.5 cm. |
| Plant width. | 40.2 cm. | 112.6 cm. |
| General coloration of the petiole. | Greyed-red. | Yellow-green. |
| General coloration of the juvenile foliage. | Green. | Maroon. |
| General coloration of the abaxial surface of the mature foliage. | Green. | Yellow-green and heavily suffused with a mixture of copper and burgundy. |

That which is claimed is:

1. A new and distinct variety of *Philodendron* plant named 'FLOPHI1901', substantially as described and illustrated herein.

* * * * *